US008715722B2

(12) United States Patent
Buydts et al.

(10) Patent No.: US 8,715,722 B2
(45) Date of Patent: May 6, 2014

(54) CAPSULE WITH AIR-VENTS

(75) Inventors: Hilde Buydts, Bornem (BE); Jan Donaat Sinnaeve, Bornem (BE); Stefaan Jaak Vanquickenborne, Bornem (BE)

(73) Assignee: Capsugel Belgium NV, Bornem (BE)

( * ) Notice: Subject to any disclaimer, the term of this patent is extended or adjusted under 35 U.S.C. 154(b) by 54 days.

(21) Appl. No.: 12/991,950

(22) PCT Filed: May 7, 2009

(86) PCT No.: PCT/IB2009/051880
§ 371 (c)(1),
(2), (4) Date: Nov. 10, 2010

(87) PCT Pub. No.: WO2009/138920
PCT Pub. Date: Nov. 19, 2009

(65) Prior Publication Data

US 2011/0064802 A1 Mar. 17, 2011

Related U.S. Application Data

(60) Provisional application No. 61/052,277, filed on May 12, 2008.

(51) Int. Cl.
*A61K 9/48* (2006.01)

(52) U.S. Cl.
USPC .......................................................... 424/454

(58) Field of Classification Search
None
See application file for complete search history.

(56) References Cited

U.S. PATENT DOCUMENTS 5,769,267 A * 6/1998 Duynslager et al. .......... 220/691
2007/0036830 A1 * 2/2007 Vanquickenborne et al. 424/400
2007/0184077 A1 8/2007 Vanquickenborne et al. 424/400

FOREIGN PATENT DOCUMENTS

WO WO9717049 5/1997 ................ A61J 3/07

OTHER PUBLICATIONS

Stegemann, S. Hard gelatin capsules today—and tomorrow. Capsugel, 2nd edition, 2002.*

* cited by examiner

*Primary Examiner* — Robert A Wax
*Assistant Examiner* — Jessica Worsham
(74) *Attorney, Agent, or Firm* — Finnegan, Henderson, Farabow, Garrett & Dunner, LLP

(57) ABSTRACT

The invention relates to a capsule comprising a hollow tubular body (2), a hollow cap (3) telescopically engageable on the body (2), the body (2) and the cap (3) defining an inner volume therebetween and being provided with complementary snap-fit means (12, 21) for locking the cap (3) on the body (2) in the fully closed final position, the complementary snap-fit means (12, 21) comprising a locking ring (12) formed on the body (2) and a complementary ridge member (21) formed on the cap (3), at least one air-vent (14) formed as an axial recess on the outer surface of the body (2) and suitable for ensuring fluid communication between the inner volume and the atmosphere. The capsule (1) is configured such that, in the fully closed final position, the inner surface of the cap (3) fits on the outer surface of the body (2) over a continuous circumferential contact section (33) and the air-vent (14) axially extends from the open end (5) of the body (2) toward the contact section (33), so as to provide fluid communication between the inner volume and the atmosphere over the whole range of engagement positions, excluding the fully closed final position wherein the inner surface of the cap (3) sealingly engages the outer surface of the body (2) over the contact section (33). Application to capsules for liquid dosages.

10 Claims, 5 Drawing Sheets

CAPSULE WITH AIR-VENTS

BACKGROUND OF THE INVENTION

The invention relates to a hard-shell capsule of a type used to deliver dosages of pharmaceuticals, medicines, vitamins, dietary supplements, etc. . . . to an individual. The invention is suitable for any dosage form but is most particularly adapted to liquid dosages.

In general, hard-shell capsules are made of two separately moulded parts, namely a body and a cap. In the manufacturing process, the cap is placed on the body in a pre-closed position providing a sufficient retention force for the transfer of pre-assembled capsules to the filling machine with no risk of separation.

In the filling machine, successive capsules are automatically processed according to the following steps:

the cap is removed from the body;

the body is filled with a dosage;

the cap is positioned again on the body and locked in a fully closed final position.

In the fully closed final position, the force to disengage the cap from the body is much higher than in the pre-closed position.

During the final joining of the capsules after filling, there is a risk that the cap is not properly fixed on the body, due to the air pressure increase inside the capsule upon closing. It is thus desirable that the air excess is allowed to escape from the inner volume of the capsule when the final assembling is processed. Therefore, it has been proposed to provide capsules with means allowing air escape.

The invention relates to such hard-shell capsules comprising:

a hollow tubular body elongated in an axial direction, having a closed end and an open end, a hollow cap slidably and telescopically engageable on the body in the axial direction from a disengaged position into a fully closed final position, the body and the cap defining an inner volume therebetween and being provided with complementary snap-fit means for locking the cap on the body in the fully closed final position, the complementary snap-fit means comprising a locking ring formed by a channel on an axial section of the body and a complementary ridge member formed on the inner surface of the cap so as to protrude inwardly, at least one air-vent formed as an axial recess on the outer surface of the body and suitable for ensuring fluid communication between the inner volume and the atmosphere over a range of engagement positions of the cap on the body.

Such a capsule is known in the prior art, for example from U.S. 2007-0184077 A1, wherein the air-vents are formed by oval dimples extending across the locking ring.

However, due to the structure of the dimples, the air escape is only allowed on a small range of engagement positions between the pre-closed position and the fully closed final position. On the remaining travel of the cap until the full engagement, the air pressure builds up in the capsule. This may cause some deformations of the capsule and the fill product, especially in case it is a liquid dosage, may leak out of the capsule before a tight sealing is made. Such leakage may occur during the transfer between the filling machine and a sealing machine, especially if the capsules are not vertically transferred.

It is an object of the invention to solve the aforementioned problem and propose a capsule design suitable to minimize the risks of leakage of the capsule after filling.

It is a further object to propose a capsule design which is adapted to the large scale manufacturing processes.

SUMMARY OF THE INVENTION

This is achieved by the hard-shell capsule according to the invention, which comprises:

a hollow tubular body elongated in an axial direction, having a closed end and an open end, a hollow cap slidably and telescopically engageable on the body in the axial direction from a disengaged position into a fully closed final position, the body and the cap defining an inner volume therebetween and being provided with complementary snap-fit means for locking the cap on the body in the fully closed final position, the complementary snap-fit means comprising a locking ring formed by a channel on an axial section of the body and a complementary ridge member formed on the inner surface of the cap so as to protrude inwardly, at least one air-vent formed as an axial recess on the outer surface of the body and suitable for ensuring fluid communication between the inner volume and the atmosphere over a range of engagement positions of the cap on the body, and is characterized in that the capsule is configured such that, in the fully closed final position, the inner surface of the cap fits on the outer surface of the body over a continuous circumferential contact section, which is axially spaced from the locking ring toward the closed end, and the air-vent axially extends from the open end of the body toward the contact section, so as to provide fluid communication between the inner volume and the atmosphere over the whole range of engagement positions, excluding the fully closed final position wherein the inner surface of the cap sealingly engages the outer surface of the body over the contact section.

A capsule according to the invention may have one or more of the following features:

the air-vent has a depth which is less than the depth of the locking ring;

the capsule comprises a plurality of such air-vents which are peripherally distributed on the body;

the air-vents are all identical and regularly distributed on the body at the same axial location;

the capsule comprises a number of such air-vents between 4 and 10, more preferably 8 such air-vents;

the capsule comprises a spray ring formed as an annular channel on the body at an axial location spaced from the locking ring toward the closed end, said spray ring defining a gap between the body and the cap when the cap is in the fully closed final position, allowing a sealing fluid to be sprayed therebetween;

the body and the cap are configured such that the cap has a stable pre-closed position on the body corresponding to a partially engaged position, wherein the effort to disengage the cap from the body is higher when the cap is in the fully closed final position than when the cap is not in the fully closed final position, e.g. when the cap is in the pre-closed position.

According to a first embodiment of the invention, the air-vent axially extends from the open end into the locking ring.

According to a second embodiment of the invention, the air-vent axially extends across the locking ring, from the open end into an area comprised between the locking ring and the contact section.

Advantageously, a capsule according to the invention may include a liquid dosage accommodated in the inner volume.

BRIEF DESCRIPTION OF THE DRAWINGS

Preferred embodiments of the invention will now be described in more details, by way of example only, with reference to the accompanying drawings, which are not drawn to scale and wherein.

DETAILED DESCRIPTION

Figure 1:
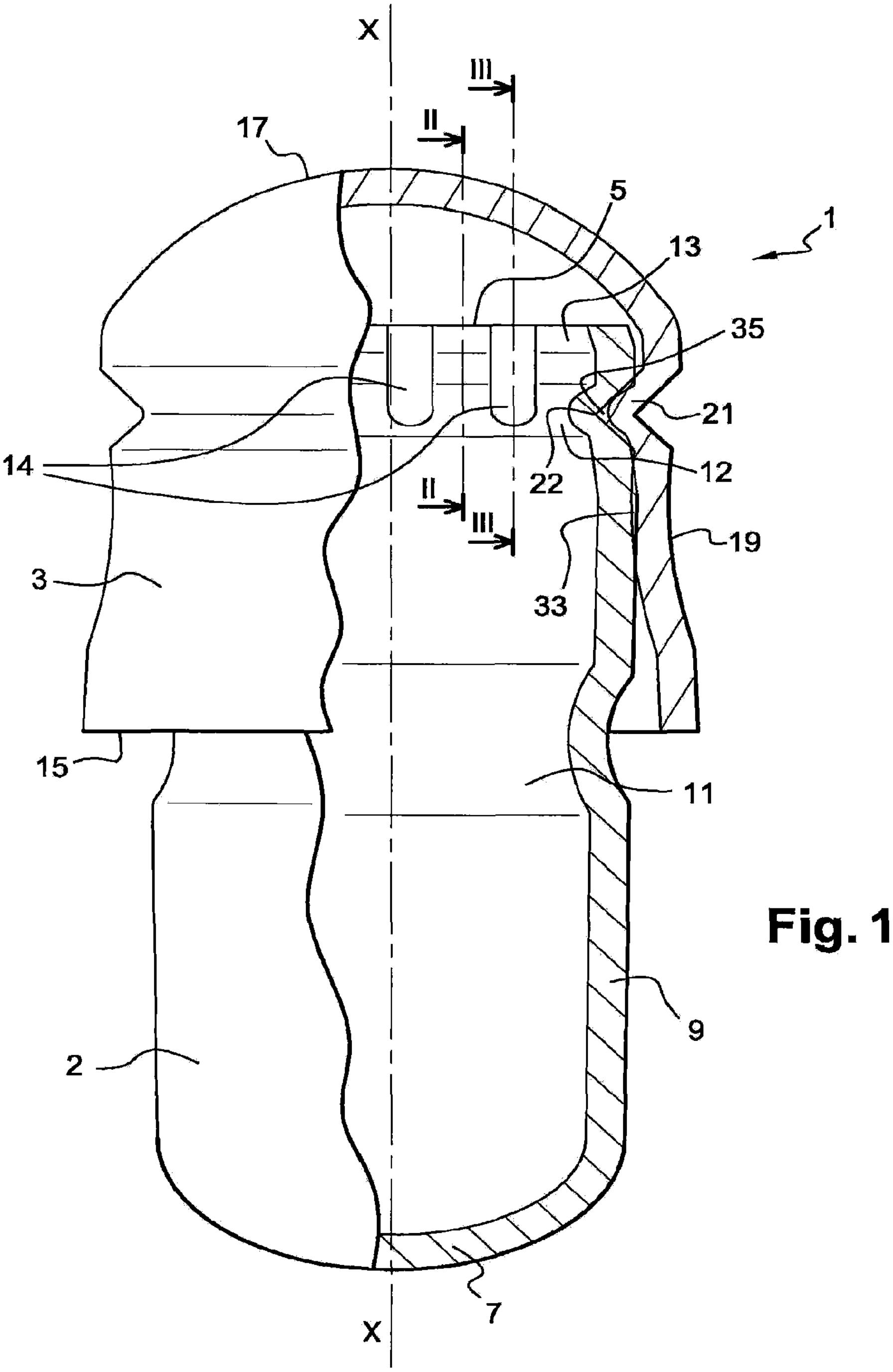
FIG. 1 is an elevation view with partial cut-away of a capsule according to a first embodiment of the invention, the capsule being in its fully closed final position.

Referring to FIG. 1, a hard-shell capsule 1 is shown as first illustrative embodiment of the present invention. The capsule 1 comprises a hollow tubular body 2 and a hollow cap 3, each being typically made in one piece by moulding from a material such as gelatine or any other pharmaceutically acceptable material. For the sake of clarity, the represented capsule is not true to scale and the curved shapes of the walls as well as the dimensions of the recessed or protruding portions are emphasized.

The body 2 and the cap 3 are adapted to be telescopically joined by partial insertion of the body 2 into the cap 3 until a fully closed or engaged final position and thus define a closed inner volume therebetween for accommodating a dosage. The herein described invention is most particularly adapted to liquid dosages but is suitable for any other dosage form, such as powder.

The tubular body 2 is elongated in an axial direction, corresponding to the insertion axis X-X, and has an open end 5 and a closed end 7. In the example shown, the body 2 includes a generally cylindrical wall 9 axially extending from the open end 5 to the closed end 7. The generally cylindrical wall 9 is circular in cross-section, although it may have various shapes in cross-section such as oval, and the closed end 5 is dome-shaped although it may also have various shapes. In particular embodiments, the closed end 5 may be hemispherical in shape.

The body 2 has an annular channel formed as a narrowed portion on an intermediate section of the cylindrical wall 9. This annular channel constitutes a spray ring 11 which defines a gap between the body 2 and the cap 3 in the fully closed final position for allowing a sealing fluid to be sprayed between the body and the cap, i.e. in an overlap region of the body and the cap.

The cylindrical wall 9 of the body 2 comprises a further narrowed portion (or channel), formed over an axial section of the body located between the spray ring 11 and the open end 5. This narrowed portion constitutes a locking ring 12 for receiving a complementary member of the cap 3, as it will be described in the following.

As visible on FIG. 1, the body 2 preferably includes an inward taper 13 at its open end 5, whereby the insertion of the body 2 into cap 3 is facilitated. The taper 13 defines a substantially conical surface for guiding the cap 3 during insertion.

The body 2 further comprises air-vents 14 formed as axial recesses on the outer surface of the body so as to ensure fluid communication between the inner volume and the atmosphere during the closure of the capsule, as it will be explained in more details in the foregoing.

Similarly to the body 2, the cap 3 has an open end 15, a closed end 17 and a generally cylindrical wall 19 extending therebetween. The generally cylindrical wall 19 has a corresponding shape to the body 2 such that the cap 3 can be slidably and telescopically engaged on the body 2 in the axial direction X-X from a disengaged position into the fully closed final position—shown on FIG. 1—. In particular, the open end 15 of the cap is generally circular in-cross section and of a slightly larger diameter than open end 5 of the body, whereby the body 2 can be inserted in the cap 3 through the open end 15.

The cap 3 includes an annular ridge 21 inwardly protruding from the generally cylindrical wall 19. The annular ridge 21 radially extends with respect to the common insertion axis X-X. In the example shown, the annular ridge 21 has an overall V-shape in cross-section and the locking ring 12 is substantially U-shaped in cross-section with a depth $d_1$, both being adapted to mutual engagement with close fit. The depth $d_1$ of the locking ring 12 is defined as the radial distance between the bottom surface of the locking ring and the outer generally cylindrical surface of the wall 9. The mutual engagement of the locking ring 12 and ridge 21 is obtained by an elastic deformation of the cylindrical walls 9, 19 during the insertion of the body 2 in the cap 3. The diameter of the ridge 21, defined as the distance between the apex 22 of the V-shaped cross-section and the axis X-X, is slightly smaller than the inner diameter of the bottom surface of the locking ring 12, whereby the ridge 21 and the locking ring 12 are resiliently biased into mutual engagement. In this respect, the locking ring 12 and the ridge 21 constitute complementary snap-fit means for locking the cap 3 on the body 2 in the fully closed final position. For the sake of clarification, the locking ring 12 and the ridge 21 need not to be identical in shape or size to define complementary snap-fit means, but rather need to be compatible in shape and size for mutual engagement with close fit.

The ridge 21 is preferably continuous along an inner circumference although it could be envisaged to provide a segmented ridge instead.

On FIG. 1, 2B, 3B, showing the capsule 1 in the fully closed final position, the actual resilient deformation of the walls 9, 19 allowing the engagement of the ridge 21 in the locking ring 12 and producing a retention force after engagement is not represented. The body 2 and the cap 3 are rather fictitiously represented in non-deformed conditions, such that these Figures show the ridge 21 and the locking ring 12 interpenetrating, which is of course not true to the actual position. The same remark applies to FIGS. 4 and 5B.

Figure 2A:
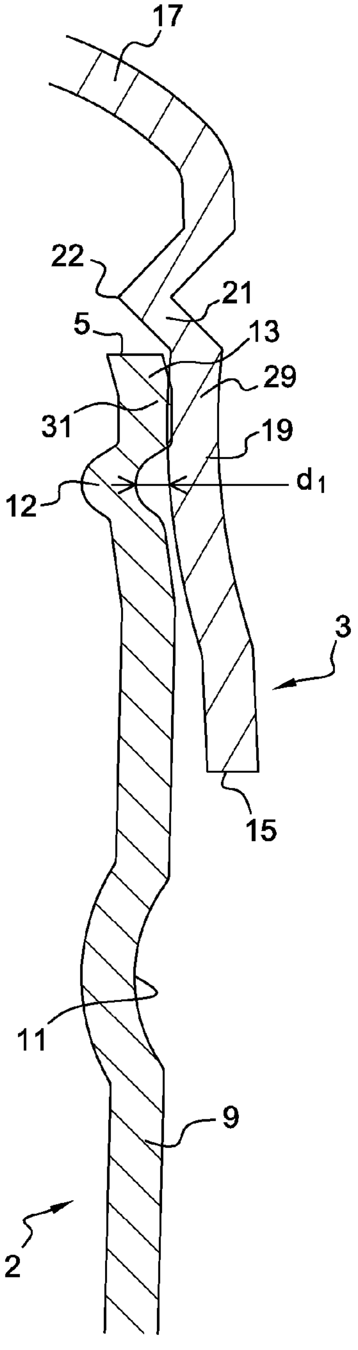
FIGS. 2A and 2B are enlarged partial cross-sectional views of the capsule of FIG. 1, along the line II-II indicated on FIG. 1, respectively in pre-closed and fully closed final positions.
Figure 3A:
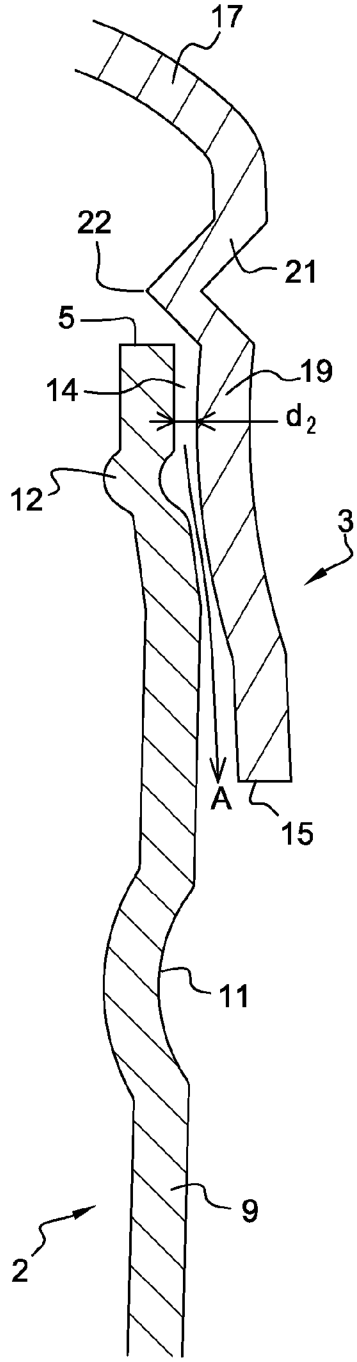
FIGS. 3A and 3B are similar views, along the line III-III indicated on FIG. 1, respectively in pre-closed and fully closed final positions.

The body 2 and the cap 3 are also configured such that the cap has a stable pre-closed position on the body, corresponding to a partially engaged position shown on FIGS. 2A and 3A. To this effect, as better seen on FIG. 2A, the inner surface of the generally cylindrical wall 19 is inwardly curved on an axial section 29 comprised between the ridge 21 and the open end 15, so as to interfere with a section 31 of the wall 9 comprised between the open end 5 and the locking ring 12. The sections 29, 31 interfere in that the inner diameter of the section 29 is slightly smaller than the outer diameter of the section 31, whereby they come into mutual engagement with resilient deformation and frictional effort. This frictional effort on the contact area between the sections 29, 31 substantially corresponds to the effort necessary to separate the cap 3 from the body 2 from this "pre-lock" or "pre-closed" position. As explained in the background section of the present description, it is significantly lower than the effort necessary to separate the cap from the body from the fully closed final position. Preferably, the ratio of these two effort values (effort from pre-closed position/effort from closed position) is in the range of 2 to 6%. The frictional effort corresponding to the pre-closed position is also a peak retention effort against the relative engagement positions of body and cap, until the fully closed final position is reached. In other words, excluding the fully closed final position, the effort to disengage the cap is maximal in the pre-closed position.

Again, on FIG. 2A, the body 2 and the cap 3 are represented in non-deformed conditions and the contact area between the sections 29, 31 is fictitiously figured by intersecting volumes.

Figure 2B:
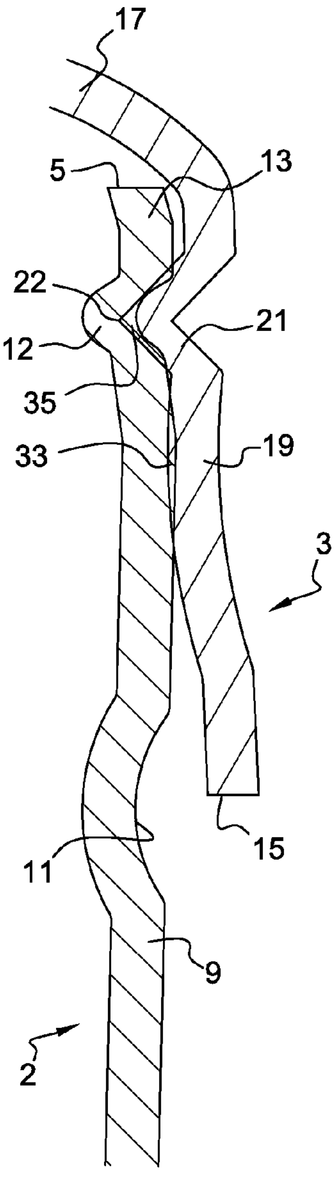
Figure 3B:
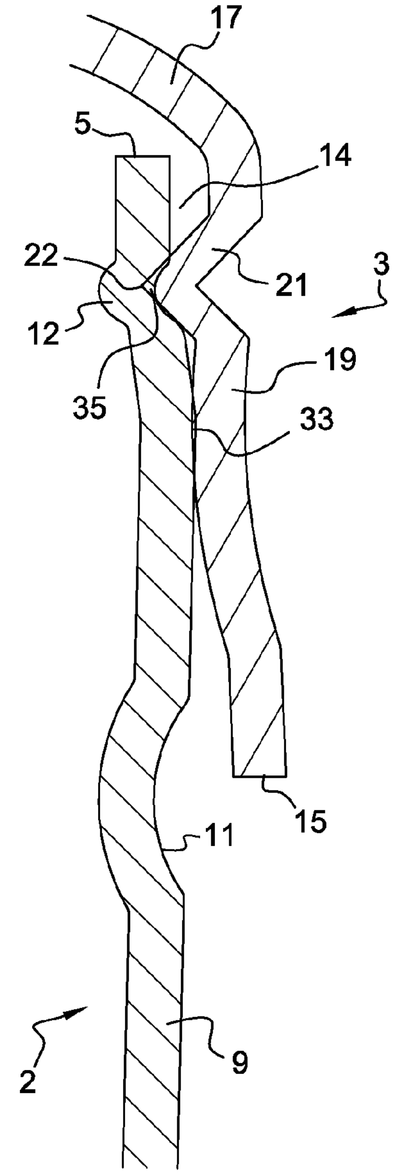

Referring now to FIG. 1, 2B and 3B, it should be noted that in the fully closed final position, the wall 19 of the cap sealingly engages the wall 9 of the body with a close fit over a continuous circumferential contact section 33 providing a provisional sealed joint between the body and the cap. By "provisional sealed joint", it is meant that the body and the cap are joined together in such a manner that no air can escape from the inner volume of the capsule and that any leakage of liquid (or eventually any other dosage form) filled in the capsule is prevented in usual manufacturing conditions. In particular, the provisional joint ensures that no leakage is permitted in a transfer line between a filling machine, wherein the capsules are filled and fully closed, and a sealing machine, wherein the capsules are definitely sealed by application of a sealing fluid, e.g. by spraying a sealing fluid in the region of the overlap of the body and the cap.

As more specifically visible on FIGS. 2B and 3B, the contact section 33 is axially spaced from the locking ring 12 toward the closed end 7 of the body.

The air-vents 14 are axially elongated and extend from the open end 5 toward the contact section 33 into the locking ring 12, whereby they do not interfere with the contact section 33. In other words, in the fully closed final position, the contact section 33 is not interrupted by any air-vent 14 along the circumference of body 2.

It should be noted that each air-vent 14 has a depth $d_2$—defined as the radial distance between the bottom surface of the air-vent and the outer generally cylindrical surface of the wall 9—which is less than the depth $d_1$ of the locking ring. The locking ring 12 is thus recessed within the recess formed by the air-vent 14. Due to this feature, the contact area 35 between the body 2 and the cap 3 defined by engagement of the ridge 21 within the locking ring 12 in the fully closed final position is not interrupted by the air-vents 14. Similarly to the contact section 33, this contact area 35 is continuous over the periphery of the body 2 in the closed position and not bypassed by the air-vents 14.

Although the body 2 could be provided with one single air-vent, the body 2 is preferably provided with a plurality of air-vents 14, as shown on the Figures representing preferred embodiments, which are peripherally distributed on the body. More preferably, the air-vents 14 are all identical, formed at the same axial location, and regularly distributed (at even angle) around the axis X-X. This permits to obtain an even distribution of the efforts and stresses on the capsule parts due to the air pressure build-up during joining, and thus minimize the risks of unwanted deformations.

It has been determined that a preferred number of such air-vents 14 on the body is within the range of 4 to 10, and most preferably equal to 8.

With reference to FIG. 2A, 2B, 3A, 3B, the function of the air-vents 14 will now be explained with more details.

As previously explained, the manufacturing process of the capsule 1 typically comprises, after the step of separately moulding the body 2 and the cap 3, a step of placing these two parts 2, 3 in a pre-closed position—illustrated on FIGS. 2A and 3A—for safe transfer to a filling station. In the filling station, the capsule 1 is reopened by separation of the capsule parts 2, 3 (by application of a relatively low separation effort). The body is kept in a vertical position, filled with the dosage (with liquid dosage in the most advantageous applications of the invention), and then the cap 3 is re-engaged on the body 2 to the fully closed final position—illustrated on FIG. 1, 2B, 3B—.

As visible on FIG. 2A, in the pre-closed position, the cap 3 and the body 2 are in mutual engagement over a contact surface defined by the respective contacting sections 29, 31. This contact surface is circumferentially interrupted (FIG. 3A) by the presence of the recessed portions constituted by the air-vents 14. Such discontinuities of the contact surface provide passages of air—represented by the arrow A—between the inner volume of the capsule and the atmosphere.

During the closure of the capsule 1 after filling, i.e. in the process of moving the cap 3 on the body 2 from the pre-closed position (FIG. 2A, 3A) into the fully closed final position (FIG. 2B, 3B), the ridge 21 slides first on the taper 13, the wall 19 thus progressively elastically expanding and generating a reaction force biasing the ridge 21 against the body 2, and then slides on the cylindrical section 31 of the wall 9. In the area of the recessed portions formed by the air-vents 14, the cap 3, including the ridge 21 and the wall 19, remains in a spaced relationship from the outer surface of the body 2 until the ridge 21 falls in the locking ring 12 due to the snap-fit effect. In this fully closed final position, as previously explained, the inner surface of the cap 3 sealingly engages the outer surface of the body 2 over the contact section 33. The contact area 35 between the locking means 12, 21 also provides an air barrier. In other words, over the whole range of engagement positions, in particular between the pre-closed position and the fully closed final position, excluding the fully closed final position, there is a gap between the body 2 and the cap 3 in the area of each air-vent 14. This gap provides a fluid communication between the inner volume and the atmosphere thus allowing the air to escape as the pressure builds-up in the capsule.

The air escape is allowed until a very late stage of mutual engagement i.e. until the ridge 21 falls into the locking ring 12, while the capsule 1 is very efficiently closed and made air-tight as soon as the closed position is reached. This is very beneficial for ensuring both that the capsule will not be leaking during the transfer to a sealing machine and that no deformation (and subsequently leak) will occur at a later stage due to the pressure build-up in the capsule.

Once filled and closed as described above, the capsule is ready for transfer to a sealing machine. As visible on FIG. 1, 2B, 3B illustrating the capsule in its fully closed final position, a sealing fluid can be easily sprayed toward the contact section 33, in the overlap of the body and cap. The spraying operation is facilitated by the presence of the spray ring 11 at the open end 15 of the cap 3 and in the vicinity of the contact section 33. The gap existing between the body and cap at the open end thereof can thus be made accessible to spray nozzles (not shown on the Figures).

Figure 4:
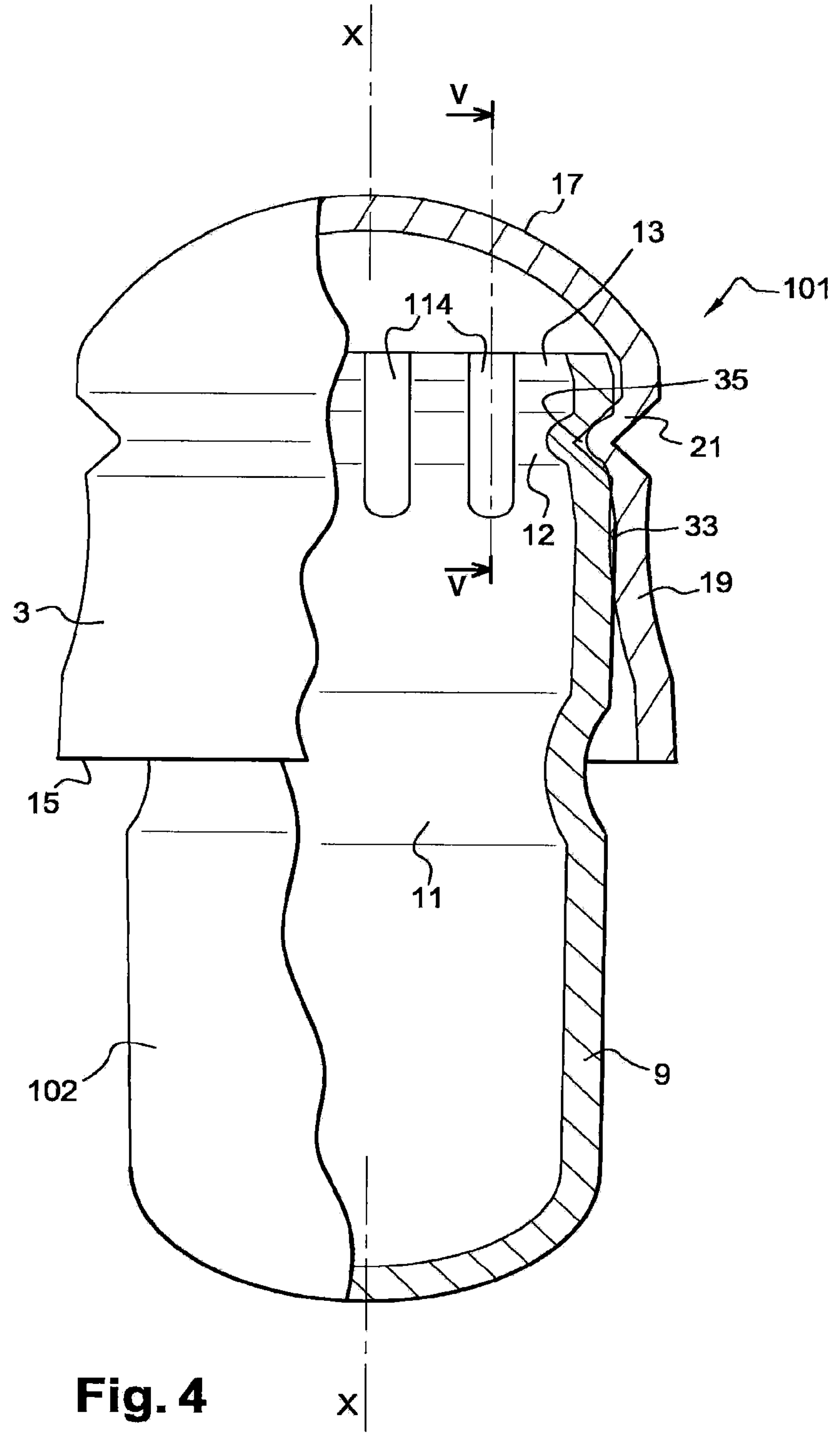
FIG. 4 is a similar view to FIG. 1 of a capsule according to a second embodiment of the invention.
Figures 5A, 5B:
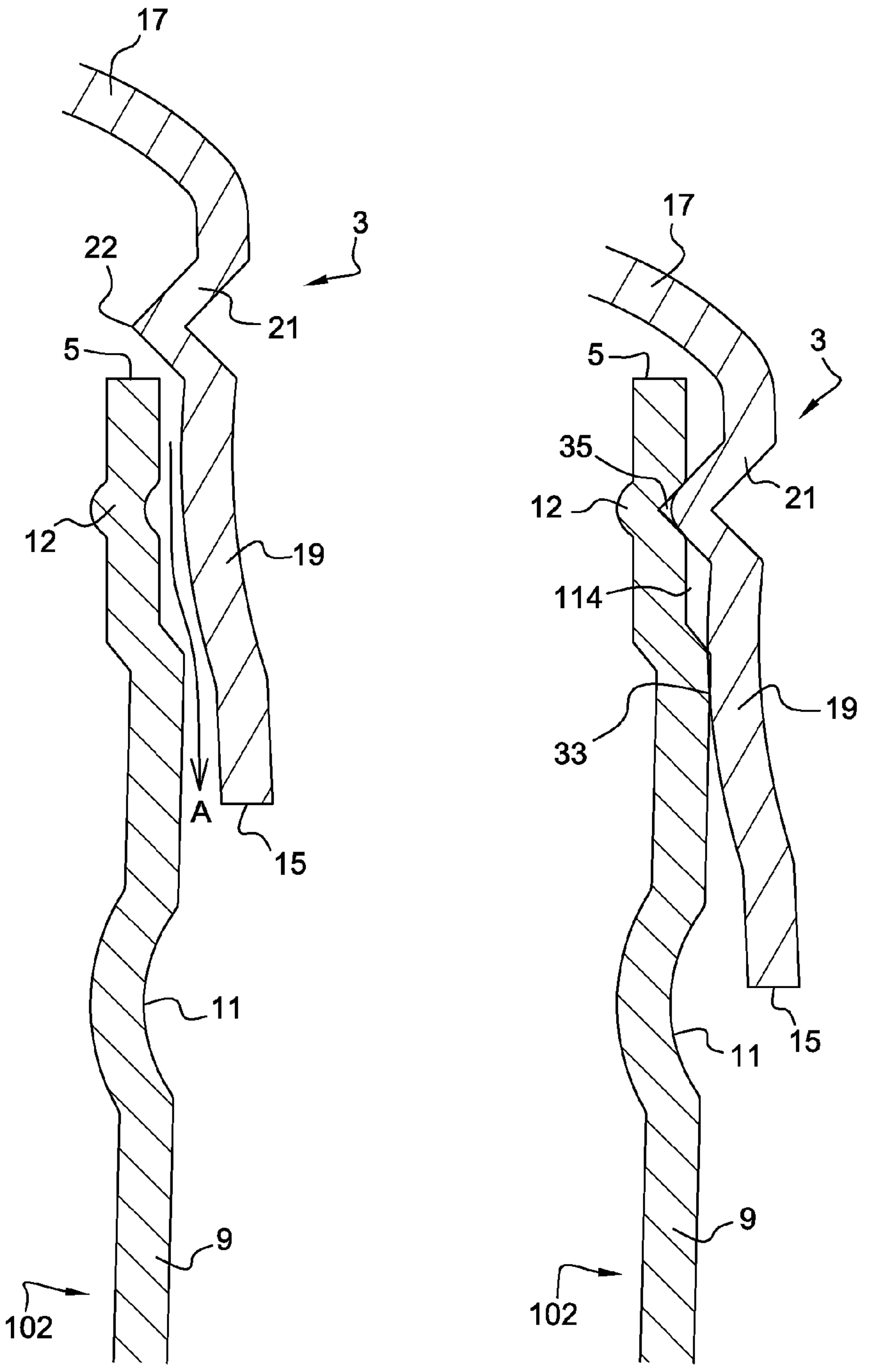
FIGS. 5A and 5B are enlarged partial cross-sectional views of the capsule of FIG. 4, along the line V-V indicated on FIG. 4, respectively in pre-closed and fully closed final positions.

A second illustrative embodiment of the invention is shown on FIG. 4, 5A, 5B. This embodiment consists in the hard-shell capsule now referred to as 101.

This embodiment only differs from the first one in that the body 102 of the capsule 101 has air-vents 114 which axially extend across the locking ring 12, from the open end 5 of the body 102 into an area comprised between the locking ring 12 and the contact section 33. Although they are of an increased length by comparison with the air-vents 14, the air-vents 114 are similarly designed so as to not interfere with the contact surface 33. It means that the contact surface 33 is continuous over the circumference of the body 102 and not interrupted by the air-vents 114. This is made clear on FIG. 5B, which shows a partial cross-sectional view of the capsule 101 in its fully closed final position, in a plane passing through an air-vent 114.

It will be appreciated that the other features of the capsule described with reference to the first embodiment may similarly apply to this second embodiment and need not to be repeated. This is also the case for the description of the air-vents function, which is similar to the description made with reference to the first embodiment and will accordingly not be repeated.

The invention claimed is:

1. A hard-shell capsule comprising:

a hollow tubular body elongated in an axial direction, having a closed end and an open end, a hollow cap slidably and telescopically engageable on the body in the axial direction from a disengaged position into a fully closed final position, the body and the cap defining an inner volume therebetween and having a complementary snap-fit means for locking the cap on the body in the fully closed final position, the complementary snap-fit means comprising a locking ring formed by a channel on an axial section of the body, and a complementary ridge member formed on the inner surface of the cap so as to protrude inwardly, at least one air-vent formed as an axial recess on the outer surface of the body configured to allow air communication between the inner volume and the atmosphere over a range of engagement positions of the cap on the body, wherein the range of engagement positions includes a position when the cap first engages with the body to at least a pre-closed position, and excludes the fully closed final position in which the inner surface of the cap sealingly engages the outer surface of the body over a continuous circumferential contact section, wherein the capsule is configured such that, in the fully closed final position, the inner surface of the cap fits on the outer surface of the body over the continuous circumferential contact section, which is axially spaced from the locking ring toward the closed end, wherein the at least one air-vent axially extends from the open end of the body toward the contact section, and wherein the at least one air-vent depth is less than the locking ring depth.

2. A capsule according to claim 1, wherein the at least one air-vent comprises a plurality of air-vents peripherally distributed on the body.

3. A capsule according to claim 2, wherein the plurality of air-vents are identical and evenly distributed at an axial location on the body.

4. A capsule according to claim 3, wherein the plurality of air-vents includes between four and ten air-vents.

5. A capsule according to claim 1, wherein the capsule further comprises a spray ring formed as an annular channel on the body at an axial location spaced from the locking ring toward the closed end, the spray ring defining a gap between the body and the cap when the cap is in the fully closed final position, allowing a sealing fluid to be sprayed therebetween.

6. A capsule according to claim 1, wherein the body and the cap are configured such that the pre-closed position is a stable pre-closed position of the cap on the body corresponding to a partially engaged position, and wherein a force to disengage the cap from the body is higher when the cap is in the fully closed final position than when the cap is not in the fully closed final position.

7. A capsule according to claim 1, wherein the at least one air-vent axially extends from the open end into the locking ring.

8. A capsule according to claim 1, wherein the at least one air-vent axially extends across the locking ring, from the open end into an area between the locking ring and the contact section.

9. A capsule according to claim 1, wherein the capsule includes a liquid dosage accommodated in the inner volume.

10. The capsule according to claim 4, wherein the plurality of air-vents includes eight air-vents.

* * * * *